(12) United States Patent
Chewter et al.

(10) Patent No.: US 8,889,941 B2
(45) Date of Patent: *Nov. 18, 2014

(54) PROCESS FOR PREPARING LOWER OLEFINS FROM AN OXYGENATE

(71) Applicant: Shell Oil Company, Houston, TX (US)

(72) Inventors: Leslie Andrew Chewter, Amsterdam (NL); Rajaram Ramesh, Amsterdam (NL); Jeroen Van Westrenen, Amsterdam (NL)

(73) Assignee: Shell Oil Company, Houston, TX (US)

( * ) Notice: Subject to any disclaimer, the term of this patent is extended or adjusted under 35 U.S.C. 154(b) by 40 days.

This patent is subject to a terminal disclaimer.

(21) Appl. No.: 13/727,877

(22) Filed: Dec. 27, 2012

(65) Prior Publication Data
US 2013/0172645 A1 Jul. 4, 2013

(30) Foreign Application Priority Data
Dec. 28, 2011 (EP) .................................... 11195850

(51) Int. Cl.
| | | |
|---|---|---|
| *C07C 1/22* | (2006.01) | |
| *C07C 41/06* | (2006.01) | |
| *C07C 1/20* | (2006.01) | |
| *C07C 7/08* | (2006.01) | |

(52) U.S. Cl.
CPC . *C07C 1/22* (2013.01); *C07C 41/06* (2013.01); *C07C 1/20* (2013.01); *C07C 7/08* (2013.01); C07C 2529/40 (2013.01); C07C 2529/70 (2013.01)
USPC ............ 585/639; 585/638; 585/640; 585/315

(58) Field of Classification Search
USPC ......... 585/314, 315, 324, 639, 752, 733, 435; 549/529, 523; 568/907
See application file for complete search history.

(56) References Cited

U.S. PATENT DOCUMENTS

| | | | | |
|---|---|---|---|---|
| 4,036,905 | A | * | 7/1977 | Kornfeld ........................ 585/639 |
| 4,513,153 | A | * | 4/1985 | Sandrin ......................... 568/697 |
| 7,439,413 | B2 | * | 10/2008 | Malzkorn et al. ............. 585/639 |
| 2006/0135833 | A1 | | 6/2006 | Malzkorn et al. |
| 2009/0137856 | A1 | | 5/2009 | Birke et al. |
| 2010/0129581 | A1 | * | 5/2010 | Lynch et al. ............... 428/36.92 |
| 2010/0298619 | A1 | * | 11/2010 | Chewter et al. ............... 585/639 |

FOREIGN PATENT DOCUMENTS

| | | | |
|---|---|---|---|
| EP | 0114498 B1 | * | 7/1987 |
| WO | WO2011057978 | | 5/2011 |

OTHER PUBLICATIONS

James G. Speight, "Petroleum Refinery Processes," Aug. 19, 2005, John Wiley and Sons, Kirk-Othmer Encyclopedia of Chemical Technology vol. 18, pp. 11-12.*

* cited by examiner

*Primary Examiner* — In Suk Bullock
*Assistant Examiner* — Sharon Pregler

(57) ABSTRACT

The invention relates to a process for preparing lower olefins from an oxygenate, the process comprising subjecting C4 hydrocarbons obtained in an oxygenate-to-olefins conversion step to extractive distillation to obtain a stream enriched in unsaturated C4 hydrocarbons comprising isobutene and n-butenes, and a stream enriched in saturated C4 hydrocarbons; converting the isobutene in the stream enriched in unsaturated C4 hydrocarbons into an alkyl tertiary butyl ether to obtain an isobutene-depleted unsaturated C4 hydrocarbon stream and alkyl tertiary-butyl ether; and recycling at least part of the isobutene-depleted unsaturated C4 hydrocarbon stream and/or at least part of the alkyl tertiary-butyl ether, optionally after conversion into tertiary butanol and/or isobutene, to the oxygenate-to-olefins conversion step.

15 Claims, 1 Drawing Sheet

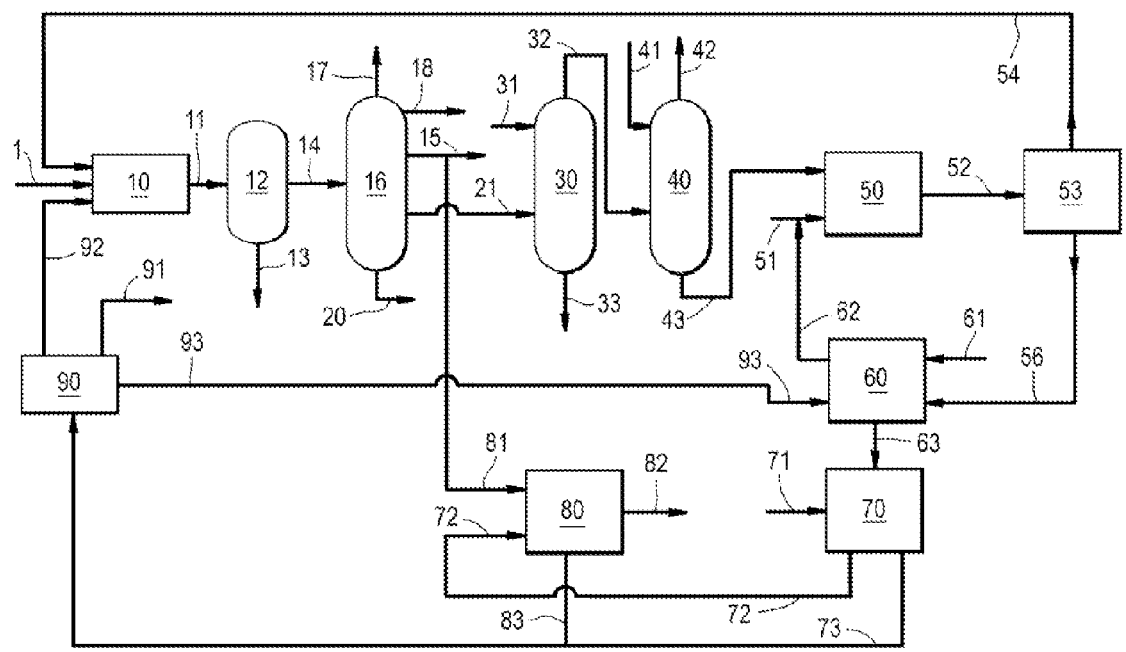

PROCESS FOR PREPARING LOWER OLEFINS FROM AN OXYGENATE

This application claims the benefit of European Patent Application No. 11195850.0, filed Dec. 28, 2011, the entire disclosure of which is hereby incorporated by reference.

FIELD OF THE INVENTION

The invention relates to a process for preparing lower olefins from an oxygenate.

BACKGROUND TO THE INVENTION

Conventionally, lower olefins such as ethylene and propylene are produced via steam cracking of hydrocarbon feedstocks including ethane, propane, naphtha, gasoil and hydrowax. An alternative route to lower olefins is the so-called oxygenate-to-olefin process. In such oxygenate-to-olefin process, an oxygenate such as methanol or dimethylether (DME) is provided to a reaction zone containing a suitable oxygenate conversion catalyst, typically a molecular sieve-comprising catalyst, and converted into ethylene and propylene. In addition to the desired lower olefins, a substantial part of the oxygenate is converted into C4+ olefins and paraffins.

In WO2009/065848 is disclosed an oxygenate-to-olefin process wherein the yield of lower olefins is increased by recycling a fraction comprising C4+ olefins to the reaction zone. At least part of the C4+ olefins in the recycle are converted into the desired lower olefins. A disadvantage of the process of WO2009/065848 is, however, that at least part of the recycle stream needs to be purged in order to avoid undesired accumulation of paraffins in the recycle stream. With the purge, also valuable C4+ olefins will be removed from the process without being converted into lower olefins.

In U.S. Pat. No. 7,923,591 is disclosed a process for manufacturing lower olefins from an oxygenate-containing reaction mixture, wherein a product stream comprising C4 and C5 hydrocarbons from the oxygenate conversion step is subjected to extractive distillation to separate saturated butanes from it. The remaining butenes and C5 hydrocarbons are, after solvent stripping, recycled to the oxygenate conversion step.

SUMMARY OF THE INVENTION

It has now been found that by subjecting a fraction comprising C4 hydrocarbons from the effluent of an oxygenate-to-olefin step to extractive distillation for separation into saturated and unsaturated C4 hydrocarbons and then subjecting the unsaturated C4 hydrocarbons to an etherification step for conversion of the isobutene into an alkyl tertiary butyl ether, it is possible to recycle butenes to the oxygenate-to-olefin step without undesired accumulation of paraffins. Moreover, by subjecting the butenes separated by the extractive distillation step to an etherification step that selectively converts isobutene, a separation between normal and isobutene has been effected. Thus, the ratio of normal and isobutene to be recycled to the oxygenate-to-olefin step can be controlled. Isobutene may be recycled in the form of the alkyl tertiary butyl ether produced in the etherification step, in the form of a tertiary butanol produced from the alkyl tertiary butyl ether, or in the form of isobutene produced from such tertiary butanol or such alkyl tertiary butyl ether. Under the reaction condition prevailing in an oxygenate-to-olefin step, tertiary butanol or alkyl tertiary butyl ether will typically be converted into isobutene.

Accordingly, the present invention relates to a process for preparing lower olefins from an oxygenate, the process comprising the following steps:
a) contacting the oxygenate with a molecular sieve-comprising catalyst, at a temperature in the range of from 350 to 1000° C. to obtain an olefinic product stream comprising ethylene, propylene and C4 hydrocarbons;
b) separating ethylene and/or propylene and a fraction comprising C4 hydrocarbons including saturated and unsaturated C4 hydrocarbons, from the olefinic product stream;
c) subjecting at least part of the fraction comprising C4 hydrocarbons to extractive distillation to obtain a stream enriched in unsaturated C4 hydrocarbons comprising isobutene and n-butenes, and a stream enriched in saturated C4 hydrocarbons;
d) supplying at least part of the stream enriched in unsaturated C4 hydrocarbons obtained in step c) and an alcohol selected from the group consisting of methanol, ethanol and a mixture thereof, to an etherification reaction zone comprising an etherification catalyst and reacting, in the etherification reaction zone, at least part of the isobutene in the stream enriched in unsaturated C4 hydrocarbons with the alcohol to obtain an etherification product stream comprising alkyl tertiary butyl ether;
e) separating the etherification product stream into an alkyl tertiary butyl ether-enriched stream and an isobutene-depleted unsaturated C4 hydrocarbon stream; and
f) recycling at least part of the isobutene-depleted unsaturated C4 hydrocarbon stream and/or at least part of the alkyl tertiary-butyl ether to step a).

The stream enriched in saturated C4 hydrocarbons obtained in step c) can advantageously be supplied to for example a steam cracking process, an LPG bleeding pool or to an isomerisation process for conversion into isobutane.

It has the further advantage that a normal butene product, depleted in iso-olefins and paraffins may be retrieved as a product stream. This can suitably be used for instance an alkylation process. Alternatively, or even additionally, it is possible to retrieve a MTBE product stream. Such a stream may suitably be used in a process for producing propylene oxide.

BRIEF DESCRIPTION OF THE DRAWING

The FIGURE schematically shows a process according to the invention.

DETAILED DESCRIPTION OF THE INVENTION

In the process according to the invention, an oxygenate is first converted into lower olefins by contacting the oxygenate with a molecular sieve-comprising catalyst at a temperature in the range of from 350 to 1000° C. (oxygenate conversion step a)). Besides lower olefins, i.e. ethylene and propylene, C4 olefinic and paraffinic hydrocarbons and, in a lesser amount C5+ olefinic and paraffinic hydrocarbons are formed as by-product. Thus, an olefinic product stream comprising ethylene, propylene, C4 hydrocarbons and higher hydrocarbons is obtained in step a). Typically, C4+ paraffins such as isobutane, n-butane, n-pentane, iso-pentane, and C4+ olefins such as isobutene, n-butenes, n-pentenes, iso-pentenes and C5+ naphtenes such as cyclopentane and cyclopentene will be present in the olefinic product stream. Small amounts of dienes like butadienes may be present in the olefinic product stream.

Reference herein to an oxygenate is to a compound comprising at least one alkyl group that is covalently linked to an oxygen atom. Preferably, at least one alkyl group has up to five carbon atoms, more preferably up to four, even more preferably one or two carbon atoms, most preferably at least one alkyl group is methyl. Mono-alcohols and dialkylethers are particularly suitable oxygenates. Methanol and dimethylether or mixtures thereof are examples of particularly preferred oxygenates.

The oxygenate conversion in step a) is carried out by contacting the oxygenate with a molecular sieve-comprising catalyst at a temperature in the range of from 350 to 1000° C., preferably of from 350 to 750° C., more preferably of from 450 to 700° C., even more preferably of from 500 to 650° C. The conversion may be carried out at any suitable pressure, preferably at a pressure in the range of from 1 bar to 50 bar (absolute), more preferably of from 1 bar to 15 bar (absolute). A pressure in the range of from 1.5 to 4.0 bar (absolute) is particularly preferred.

Any molecular sieve comprising catalyst known to be suitable for the conversion of oxygenates, in particular alkanols and dialkylethers, into lower olefins may be used. Preferably the catalyst comprises a molecular sieve having a 8-, 10- or 12-ring structure and an average pore size in the range of from 3 Å to 15 Å. Examples of suitable molecular sieves are silicoaluminophosphates (SAPOs), aluminophosphates (AlPO), metal-substituted aluminophosphates or metal-substituted silicoaluminophosphates. Preferred SAPOs include SAPO-5, -8, -11, -17, -18, -20, -31, -34, -35, -36, -37, -40, -41, -42, -44, -47 and -56. SAPO-17, -18, -34, -35, and -44 are particularly preferred.

A particular suitable class of molecular sieves are zeolites. In particular in case not only oxygenates but also C4+ olefins or compounds that form C4+ olefins under the reaction conditions prevailing in oxygenate conversion step a) are supplied to step a), e.g. a tertiary alkylether such as methyl tertiary butylether, a zeolite-comprising catalyst is preferred as molecular-sieve comprising catalyst, more preferably a catalyst comprising a zeolite with at least a 10-membered ring structure. Zeolite-comprising catalysts are known for their ability to convert higher olefins to lower olefins, in particular C4+ olefins to ethylene and/or propylene. Suitable zeolite-comprising catalysts include those containing a zeolite of the ZSM group, in particular of the MFI type, such as ZSM-5, the MTT type, such as ZSM-23, the TON type, such as ZSM-22, the MEL type, such as ZSM-11, the FER type. Other suitable zeolites are for example zeolites of the STF-type, such as SSZ-35, the SFF type, such as SSZ-44 and the EU-2 type, such as ZSM-48. Preferably, the catalyst comprises at least one zeolite selected from MFI, MEL, TON and MTT type zeolites, more preferably at least one of ZSM-5, ZSM-11, ZSM-22 and ZSM-23 zeolites.

The zeolite in the oxygenate conversion catalyst is preferably predominantly in the hydrogen form. Preferably at least 50 wt %, more preferably at least 80 wt %, even more preferably at least 95 wt %, still more preferably at least 100 wt % of the zeolite is in the hydrogen form.

The molecular sieve-comprising catalyst may further comprise a binder material such as for example silica, alumina, silica-alumina, titania, or zirconia, a matrix material such as for example a clay, and/or a filler.

The present molecular sieve catalyst may comprise phosphorus as such or in a compound, i.e. phosphorous other than any phosphorus included in the framework of the molecular sieve. It is preferred that an MEL or MFI-type zeolite comprising catalyst additionally comprises phosphorus. The phosphorus may be introduced by pre-treating the MEL or MFI-type zeolites prior to formulating the catalyst and/or by post-treating the formulated catalyst comprising the MEL or MFI-type zeolites. Preferably, the present molecular sieve catalyst comprising MEL or MFI-type zeolites comprises phosphorus as such or in a compound in an elemental amount of from 0.05-10 wt % based on the weight of the formulated catalyst. A particularly preferred catalyst comprises phosphorus and MEL or MFI-type zeolites having SAR of in the range of from 60 to 150, more preferably of from 80 to 100. An even more particularly preferred catalyst comprises phosphorus and ZSM-5 having SAR of in the range of from 60 to 150, more preferably of from 80 to 100.

In step a), not only lower olefins and C4+ hydrocarbons, but also water is formed. Water is typically separated from the olefinic product stream by means known in the art, for example by cooling the effluent of step a) in a water quench tower.

In step b) of the process according to the invention, ethylene and/or propylene and a fraction comprising C4 hydrocarbons are separated from the olefinic product stream obtained in step a). Such separation in different fractions is done by means known in the art. Typically, the stream is fractionated in at least a fraction mainly comprising ethylene and/or propylene and a fraction comprising C4 hydrocarbons. Usually, a fraction comprising mainly ethylene is first separated from the olefinic product stream in a de-ethaniser and a fraction mainly comprising propylene is then separated from the bottoms of the de-ethaniser in a de-propaniser. Instead of fractionating the olefinic product stream into separate ethylene and propylene fractions, a fraction comprising both ethylene and propylene may be obtained by directly supplying the olefinic product stream to a de-propaniser. The bottoms of the de-propaniser contain C4+ hydrocarbons. Preferably, the bottoms of the de-propaniser is further separated into a fraction mainly comprising C4 hydrocarbons and a fraction comprising C5+ hydrocarbons. The fraction comprising C4 hydrocarbons comprises saturated and unsaturated C4 hydrocarbons. The unsaturated C4 hydrocarbons comprise isobutene and n-butenes.

In step c) at least part of the fraction comprising C4 hydrocarbons obtained in step b) is subjected to extractive distillation in order to remove saturated C4 hydrocarbons, i.e. butanes, from the C4 olefins in that fraction. Thus, a stream enriched in unsaturated C4 hydrocarbons comprising isobutene and n-butenes, and a stream enriched in saturated C4 hydrocarbons comprising normal and iso-butane, are obtained. Butadiene, if present, may be removed from the fraction comprising C4 hydrocarbons prior to subjecting the fraction to extractive distillation for removal of saturated C4 hydrocarbons.

Part of the fraction comprising C4 hydrocarbons obtained in step b) may be recycled to step a).

In step c), at least part of the fraction comprising C4 hydrocarbons is, optionally after removal of butadiene, subjected to extractive distillation. In extractive distillation step c), a stream enriched in unsaturated C4 hydrocarbons and a stream enriched in saturated C4 hydrocarbons are obtained. The extractive distillation is carried out by supplying at least part of the fraction comprising C4 hydrocarbons to an extractive distillation column together with a suitable solvent, such as for example dimethylformamide (DMF), N-formylmorpholine (NFM), acetonitrile or N-methylpyrrolidone. Saturated C4 hydrocarbons leave the column over the top and solvent containing unsaturated C4 hydrocarbons leaves the column via the bottom. In case the fraction comprising C4 hydrocarbons comprises C5+ hydrocarbons, the bottom fraction will further comprises such C5+ hydrocarbons.

Separation of butanes from butenes by means of extractive distillation is well-known in the art. Any suitable process conditions and solvents known in the art may be applied.

Solvent is separated from the butenes by means known in the art, typically by stripping, in order to obtain the stream enriched in unsaturated C4 hydrocarbons.

The prior removal of butadiene is typically done by extractive distillation. Thus, in case butadiene is removed prior to butane/butane separation, the process typically comprises two extractive distillation steps: a first extractive distillation step to remove butadiene and a second extractive distillation step to separate butenes from butanes. In the first step, the fraction comprising C4 hydrocarbons and a suitable solvent are supplied to a first extractive distillation column. A stream comprising butenes and butanes will leave the column over the top and solvent containing butadiene leaves the column via the bottom. In the second step, the stream comprising butenes and butanes is supplied together with a suitable solvent to a second extractive distillation column. The saturated C4 hydrocarbons (butanes) leave the column over the top and solvent containing unsaturated C4 hydrocarbons including isobutene and n-butenes leaves the column via the bottom. In each of the extractive distillation steps, any suitable process conditions and solvents known in the art may be applied. Preferably, the same solvent is used in both extractive distillation steps.

The stream enriched in saturated C4 hydrocarbons (top stream of the extractive distillation column) may be withdrawn from the process and for example used for steam cracking, blended into an LPG pool, or isomerised to isobutane.

In step d), at least part of the stream enriched in unsaturated C4 hydrocarbons is supplied to an etherification reaction zone together with an alcohol. The etherification zone comprises an etherification catalyst and in this zone at least part of the isobutene in the stream enriched in unsaturated C4 hydrocarbons is reacted with the alcohol to be converted into alkyl tertiary butyl ether. In case the stream enriched in unsaturated C4 hydrocarbons also comprises iso-pentenes, also alkyl tertiary amyl ether is formed. Thus, an etherification product stream comprising alkyl tertiary butyl ether is obtained. The alcohol is selected from the group consisting of methanol, ethanol and a mixture thereof. Preferably, the alcohol is methanol and an etherification product stream comprising methyl tertiary butyl ether is obtained. Etherification of isobutene to form an alkyl tertiary butyl ether is well-known in the art. Any catalyst and process conditions known to be suitable for such etherification may be used. Typically, the etherification catalyst is an acid catalyst. Preferably, the etherification catalyst is a protonated cation-exchange resin or a heteropolyacid promoted by a metal. A particularly preferred catalyst is Amberlyst-15. Preferably, the etherification reaction is carried out at a temperature in the range of from 40 to 100° C., more preferably of from 50 to 85° C. The reaction may be carried out at any suitable pressure, preferably in the range of from 1 to 20 bar (absolute), more preferably of from 5 to 15 bar (absolute).

In a subsequent step e), the etherification product stream is separated into an alkyl tertiary butyl ether-enriched stream and an isobutene-depleted unsaturated C4 hydrocarbon stream. This may be done by any suitable means known in the art, for example by distillation.

In step f), at least part of the isobutene-depleted unsaturated C4 hydrocarbon stream and/or at least part of the alkyl tertiary-butyl ether is recycled to oxygenate-to-olefin conversion step a).

Preferably at least part of the isobutene-depleted unsaturated C4 hydrocarbon stream is recycled to step a), more preferably at least 50 wt %, even more preferably at least 90 wt %. Since the isobutene-depleted unsaturated C4 hydrocarbon stream does not or hardly comprise saturated hydrocarbons, the entire isobutene-depleted unsaturated C4 hydrocarbon stream may be recycled to step a). Recycling of a stream depleted in isobutene is particularly advantageous in case a molecular sieve comprising catalyst is used in step a) that does not or does hardly catalyse the conversion of isobutene into lower olefins. Examples of such catalysts are SAPO-containing catalysts, in particular a SAPO-34 containing catalyst.

Alternatively, or in combination with a recycle of at least part of the isobutene-depleted unsaturated C4 hydrocarbon stream, at least part of the alkyl tertiary-butyl ether produced in step c) is recycled to oxygenate-to-olefin conversion step a). Such recycle of alkyl tertiary-butyl ether is advantageous in case a molecular sieve comprising catalyst is used in step a) that is able to catalyse the conversion of isobutene into lower olefins, as is typically the case for a zeolite-comprising catalyst, in particular a catalyst comprising a zeolite with a 10-membered ring structure. Alkyl tertiary-butyl ether may be recycled as such to step a) or in the form of tertiary butanol and/or isobutene, i.e. after conversion into tertiary butanol and/or isobutene.

The alkyl tertiary-butyl ether may be decomposed to back to the alcohol and the iso-olefins, or optionally the alcohol and an iso-paraffin. In that case the methanol may be recycled to the etherification process.

The alkyl tertiary butyl ether formed in step d) can advantageously be converted into tertiary butyl hydroperoxide, which can be converted into an epoxide by reacting it with ethylene and/or propylene separated from the olefinic product stream obtained in step a). Thus, an integrated process for preparing an epoxide from an oxygenate is provided. Such process further comprises: converting at least part of the alkyl tertiary butyl ether in the alkyl tertiary butyl ether-enriched stream into the alcohol and isobutane (step g)); oxidizing isobutane obtained in step g) into tertiary butyl hydroperoxide (step h)); and reacting the tertiary butyl hydroperoxide with ethylene and/or propylene separated from the olefinic product stream obtained in step a) to obtain the epoxide and tertiary butanol (step i)).

At least part of the alkyl tertiary butyl ether in the alkyl tertiary butyl ether-enriched stream may be converted into the alcohol and isobutane, for example by first cracking alkyl tertiary butyl ether into isobutene and the alcohol and then hydrogenating the isobutene thus-formed into isobutane. The cracking of a tertiary alkyl ether into its corresponding alcohol and iso-olefin and the hydrogenation of an iso-olefin into its corresponding iso-alkane are well-known in the art. The cracking and hydrogenation may be carried out in any suitable way known in the art.

Alternatively and preferably, the alkyl tertiary butyl ether is directly converted into tertiary butane and the alcohol, i.e. in a single step. The cracking and hydrogenation is then combined by contacting the alkyl tertiary butyl ether with a hydrocracking catalyst in the presence of hydrogen. Any suitable hydrocracking catalyst may be used for this step. Such catalyst comprises a hydrogenating function, preferably a hydrogenating metal, supported on an acidic support material. Preferably, the catalyst comprises an acidic support material selected from zeolitic or amorphous silica alumina and alumina. Amorphous silica alumina is a particularly preferred support material. The hydrogenation function is preferably a hydrogenating metal selected from Group VIII metals, more preferably selected from Pt, Pd, Ru, Rh, Ir, Ni and combinations thereof. Hydrogenating metal that do not easily convert methanol into carbon monoxide and hydrogen under the hydrocracking conditions prevailing in this step are particularly preferred. Examples of such hydrogenating metals are Pt and a combination of Pt and Ru.

Where the reaction product in step (a) comprises ethylene, at least part of the ethylene may be further converted into at least one of polyethylene, mono-ethylene-glycol, ethylbenzene and styrene monomer. Where the reaction product in step (a) comprises propylene, at least part of the propylene may be further converted into at least one of polypropylene and propylene oxide.

DETAILED DESCRIPTION OF THE DRAWING

In the FIGURE, an embodiment of the invention is schematically shown wherein the isobutene-depleted unsaturated C4 hydrocarbon stream and part of the alkyl tertiary butyl ether formed in step d) are recycled to step a). The alkyl tertiary butyl ether formed in step d) is recycled after conversion into tertiary butanol and further conversion into isobutene.

Methanol is fed via line 1 to oxygenate conversion reaction zone 10 comprising an oxygenate conversion catalyst. In reaction zone 10, methanol is converted into olefins and water. Effluent from reaction zone 10 is supplied via line 11 to water quench tower 12 to be separated into water and an olefinic product stream. Water is withdrawn from tower 12 via line 13 and the olefinic product stream is supplied via line 14 to fractionation section 16. Fractionation section 16 comprises a de-ethaniser, a de-propaniser and a de-butaniser (not shown). The olefinic product stream is first fractionated by means of the de-ethaniser and de-propaniser into an ethylene-rich stream, a propylene-rich stream, a C4+ hydrocarbon fraction and a lighter stream comprising light by-products such as methane and carbon oxides. The C4+ hydrocarbon fraction is further fractionated in the de-butaniser into a C4 hydrocarbon fraction comprising isobutene and a fraction rich in C5+ hydrocarbons. The lighter stream, the ethylene-rich stream, the propylene-rich stream and the fraction rich in C5+ hydrocarbons are withdrawn from fractionation section 16 via lines 17, 18, 15 and 20, respectively. The fraction comprising C4 hydrocarbons is fed via line 21 to first extractive distillation column 30. Solvent (NFM) is supplied to column 30 via line 31. A stream 33 comprising solvent and butadiene is withdrawn from the bottom of column 30, and a stream comprising butanes and butenes is withdrawn from the top of column 30 via line 32 and supplied to second extractive distillation column 40. Traces of butadiene that might be present in the top stream of column 30 may be removed by selective hydrogenation prior to supplying the top stream to second extractive distillation column 40. In column 40, the stream comprising butanes and butenes is separated into a stream enriched in butanes and a stream enriched in butenes. To column 40, NFM is supplied as solvent via line 41. A stream enriched in butanes is withdrawn from the top of column 40 via line 42 and a stream comprising NFM and butenes is withdrawn from the bottom of column 40 via line 43. After removal of the NFM (not shown) a stream enriched in butenes is supplied to etherification reaction zone 50.

Methanol is supplied via line 51 to reaction zone 50 comprising an etherification catalyst. In etherification reaction zone 50, isobutene is reacted with methanol to form methyl tert-butyl ether (MtBE). The effluent of reaction zone 50 is supplied via line 52 to separator 53 to be separated into an isobutene depleted C4 hydrocarbon stream and an MtBE-enriched stream. The isobutene depleted C4 hydrocarbon stream is recycled to reaction zone 10 via line 54. The MtBE-enriched stream is withdrawn from separator 53 via line 56 and supplied to MtBE hydrocracking zone 60. Hydrogen is supplied to hydrocracking zone 60 via line 61. In zone 60, MtBE is converted into methanol and isobutane. Methanol is recycled to etherification zone 50 via line 62. Part of the methanol may be recycled to oxygenate conversion zone 10 (recycle not shown). Isobutane obtained in zone 60 is supplied via line 63 to oxidation reaction zone 70. Air is supplied as oxidant to zone 70 via line 71. In zone 70, isobutane is oxidised to tertiary butyl hydroperoxide and tertiary butanol. The tertiary butyl hydroperoxide formed in zone 70 is supplied via line 72 to epoxidation zone 80. The tertiary butanol formed is withdrawn via line 73. Part of the propylene-rich stream separated in fractionation section 16 is supplied to zone 80 via line 81. In zone 80, propylene oxide and tertiary butanol are formed. Propylene oxide is withdrawn as product via line 82. The tertiary butanol formed is withdrawn via line 83 and, combined with the tertiary butanol in line 73, supplied to tertiary butanol dehydration zone 90 and dehydrated into isobutene. Water is withdrawn from zone 90 via line 91. Part of the isobutene thus-formed is recycled to oxygenate conversion zone 10 via line 92 and part of the isobutene is recycled to MtBE hydrocracking zone 60 via line 93.

The invention is illustrated by the following non-limiting example.

EXAMPLE

Model calculations were carried out for a process configuration as shown in the FIGURE, except that a single extractive distillation column is used (no prior removal of butadiene by extractive distillation).

A stream of 3349 kilotons per annum (kton/a) of methanol, 114 kton/a of a recycle stream of isobutene and 240 kton/a of a recycle stream of isobutene-depleted C4 hydrocarbons are supplied to oxygenate conversion zone 10. The isobutene-depleted C4 hydrocarbons stream comprises 177 kton/a of normal butenes, 53 kton/a of C4 paraffins and 10 kta of methanol. Zone 10 contains a zeolitic catalyst comprising ZSM-23 and ZSM-5 with a silica-to-almina ratio of 280 in a weight ratio of 4 to 1, a binder and matrix material. In zone 10, water and an olefinic product stream are formed. Fractionation yields 1146 kton/a of lower olefins, a C4 hydrocarbon fraction (363 kton/a) and a stream rich in C5+ hydrocarbons. The C4 hydrocarbon fraction is fed to the extractive distillation zone 40. In the extractive distillation zone, the C4 hydrocarbon fraction is contacted with NFM as solvent in a solvent to feed ratio of 5. A top product stream of 17 kton/a of C4 paraffins and 2 kton/a of C4 n-butenes is obtained. The 17 kton/a of C4 paraffin that are removed with the top stream from extractive distillation zone 40 matches the amount of C4 paraffins produced in oxygenate-to-olefins reaction zone 10. Hence, C4 paraffins are not built up in the recycle to reaction zone 10. A bottom product stream comprising solvent and 291 kton/a of n-butenes, 53 kton/a of C4 paraffins is obtained in extractive distillation zone 40. The NFM solvent is removed in a stripping zone that is not shown in the FIGURE.

After stripping, a stream enriched in unsaturated C4 hydrocarbon is obtained that contains 291 kton/a of n-butenes and 53 kton/a of C4 paraffins. This stream and 75 kton/a of methanol (65 kton/a recycled from MtBE hydrocracking zone 60 plus 10 kton/a make-up from an external methanol supply) is fed to etherification reaction zone 50 and MtBE is formed. After separation of the MtBE from the remaining C4 hydrocarbons, an azeotropic mixture of 230 kton/a of isobutene-depleted C4 hydrocarbons and 10 kton/a methanol is obtained and recycled to oxygenate-to-olefins reaction zone 10.

A stream of 179 kton/a of MtBE separated from the effluent of etherification reaction zone 50, 369 kton/a of isobutene from isobutanol dehydration zone 90, and 17 kton/a of hydrogen are fed to MtBE hydrocracking zone 60 to form 500 kton/a of isobutane and 65 kton/a of methanol. The methanol is recycled to etherification reaction zone 50. The isobutane is supplied, together with air, to oxidation reaction zone 70 to form tert-butyl hydroperoxide and tertiary butanol. The tert-butyl hydroperoxide and 181 kton/a of the propylene produced in zone 10 are converted into 250 kton/a of propylene oxide in epoxidation zone 80. The tertiary butanol formed in zones 70 and 80 is dehydrated in dehydration zone 90 to form 155 kton/a of water, and 483 kton/a of isobutene. Part of the isobutene (114 kton/a) is recycled to oxygenate conversion zone 10 and part (369 kton/a) is recycled to MtBE hydrocracking zone 60.

TABLE

Product streams in kilotons per annum in the EXAMPLE

| line | Compound | EXAMPLE |
|---|---|---|
| 1 | methanol | 3349 |
| 42 | Normal-butane and isobutane | 17 |
| 54 | isobutene-depleted C4 hydrocarbons including MeOH (azeotropic mixture) | 240 |
| 61 | hydrogen | 17 |
| 63 | isobutane | 500 |
| 81 | propylene | 181 |
| 82 | propylene oxide | 250 |
| 92 | isobutene | 114 |
| 93 | isobutene | 369 |

What is claimed is:

1. A process for preparing lower olefins from an oxygenate, the process comprising the following steps:
   a) contacting the oxygenate with a molecular sieve-comprising catalyst, at a temperature in the range of from 350 to 1000° C. to obtain an olefinic product stream comprising ethylene, propylene and C4 hydrocarbons;
   b) separating ethylene and/or propylene and a fraction comprising C4 hydrocarbons including saturated and unsaturated C4 hydrocarbons, from the olefinic product stream;
   c) subjecting at least part of the fraction comprising C4 hydrocarbons to extractive distillation to obtain a stream enriched in unsaturated C4 hydrocarbons comprising isobutene and n-butenes, and a stream enriched in saturated C4 hydrocarbons;
   d) supplying at least part of the stream enriched in unsaturated C4 hydrocarbons obtained in step c) and an alcohol selected from the group consisting of methanol, ethanol and a mixture thereof, to an etherification reaction zone comprising an etherification catalyst and reacting, in the etherification reaction zone, at least part of the isobutene in the stream enriched in unsaturated C4 hydrocarbons with the alcohol to obtain an etherification product stream comprising alkyl tertiary butyl ether;
   e) separating the etherification product stream into an alkyl tertiary butyl ether-enriched stream and an isobutene-depleted unsaturated C4 hydrocarbon stream; and
   f) recycling at least part of the isobutene-depleted unsaturated C4 hydrocarbon stream to step a).

2. A process according to claim 1, wherein at least part of the alkyl tertiary-butyl ether stream is recycled to step a).

3. A process according to claim 1, where the oxygenate is methanol, dimethylether, or a mixture thereof.

4. A process according to claim 1 wherein the oxygenate in step (a) is an alcohol and the same alcohol is used as alcohol in etherification step (d).

5. A process according to claim 1 wherein the alkyl tertiary butyl ether in the alkyl tertiary butyl ether-enriched stream is decomposed to at least an alcohol and the alcohol is recycled to step (d).

6. A process according to claim 1 further comprising:
   g) converting at least part of the alkyl tertiary butyl ether in the alkyl tertiary butyl ether-enriched stream into the alcohol and isobutane;
   h) oxidizing isobutane obtained in step g) into tertiary butyl hydroperoxide; and
   i) reacting tertiary butyl hydroperoxide obtained in step h) with ethylene and/or propylene separated from the olefinic product stream obtained in step a) to obtain an epoxide and tertiary butanol.

7. A process according to claim 6, wherein in step g) the alkyl tertiary butyl ether is first converted into isobutene and the alcohol and the isobutene is then hydrogenated into isobutane.

8. A process according to claim 6, wherein in step g) the alkyl tertiary butyl ether is directly converted into isobutane and the alcohol by contacting alkyl tertiary butyl ether with a hydrocracking catalyst in the presence of hydrogen.

9. A process according to claim 6 wherein at least part of the tertiary butanol obtained in step i) is recycled to oxygenate conversion step a).

10. A process according to claim 1 wherein the molecular sieve-containing catalyst is a zeolite-comprising catalyst.

11. A process according to claim 10, wherein the zeolite-comprising catalyst comprises at least one zeolite selected from MFI, MEL, TON and MTT zeolites.

12. A process according to claim 11, wherein the zeolite-comprising catalyst comprises at least one of ZSM-5, ZSM-11, ZSM-22 and ZSM-23 zeolites.

13. A method according to claim 1 wherein the reaction product in step (a) comprises ethylene and at least part of the ethylene is further converted into at least one of polyethylene, mono-ethylene-glycol, ethylbenzene and styrene monomer.

14. A method according to claim 1 wherein the reaction product in step (a) comprises propylene and at least part of the propylene is further converted into at least one of polypropylene and propylene oxide.

15. A method according to claim 1 wherein at least part of the stream enriched in unsaturated C4 hydrocarbons is used in at least one of a metathesis with ethylene to produce additional propylene, an alkylation process to produce alkylate and polymerization of ethylene to produce polyethylene.

* * * * *